United States Patent
Henegar

(10) Patent No.: US 6,974,834 B2
(45) Date of Patent: Dec. 13, 2005

(54) PROCESS FOR PREPARING ENANTIOMERICALLY ENRICHED (1S,4R) 1-ACETOXY-4-HYDROXYCYCLOPENT-2-ENE

(75) Inventor: Kevin Edward Henegar, Ann Arbor, MI (US)

(73) Assignee: Agouron Pharmaceuticals Inc., San Diego, CA (US)

( * ) Notice: Subject to any disclaimer, the term of this patent is extended or adjusted under 35 U.S.C. 154(b) by 0 days.

(21) Appl. No.: 10/753,136

(22) Filed: Jan. 7, 2004

(65) Prior Publication Data

US 2004/0171129 A1 Sep. 2, 2004

Related U.S. Application Data

(60) Provisional application No. 60/439,953, filed on Jan. 14, 2003.

(51) Int. Cl.$^7$ .............................................. A61K 31/21
(52) U.S. Cl. .................. 514/546; 514/529; 514/506; 514/548; 514/549; 568/591; 568/579; 435/132; 435/155
(58) Field of Search .................. 514/548, 549, 514/546, 529, 506; 568/591, 579; 435/132, 155; 425/132

(56) References Cited

FOREIGN PATENT DOCUMENTS

DE 293 136 * 8/1991 ............. C12P/7/62

OTHER PUBLICATIONS

T.T. Curran, et al., Tetrahedron, 53, 1983–2004 (1997).
S. Miura, et al., Tetrahedron, 32, 1893–1898 (1976).
F. Thiel, et al., Liebigs Ann. Chem., 195–200 (1991).
F. Thiel, et al., Synthesis, 540–541 (1988).
F. Theil, et al., Tetrahedron 47, 7569–7582 (1991).

* cited by examiner

*Primary Examiner*—Leon B. Lankford, Jr.
*Assistant Examiner*—Allison M. Ford
(74) *Attorney, Agent, or Firm*—Edward D. Robinson; Bryan C. Zielinski

(57) ABSTRACT

This invention relates to a process for the synthesis of enantiomerically enriched (1S,4R) 1-acetoxy-4-hydroxycyclopent-2-ene of Formula I, a compound useful as an intermediate in the synthesis of prostaglandins and prostanoids.

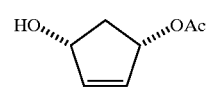

Formula I

4 Claims, No Drawings

PROCESS FOR PREPARING ENANTIOMERICALLY ENRICHED (1S,4R) 1-ACETOXY-4-HYDROXYCYCLOPENT-2-ENE

CROSS REFERENCE TO RELATED APPLICATION

This application claims the benefit of U.S. provisional application Ser. No. 60/439,953 filed on 14 Jan. 2003, under 35 USC 119(e)(i), which are incorporated herein by reference in their entirety.

FIELD OF THE INVENTION

This invention relates to a process for the synthesis of enantiomerically enriched (1S,4R) 1-acetoxy-4-hydroxycyclopent-2-ene of Formula I, a compound useful as an intermediate in the synthesis of prostaglandins and prostanoids.

Formula I

BACKGROUND

The prostaglandins are an important series of molecules that have a wide variety of uses. There are many known syntheses of prostaglandins and (1S,4R) 1-acetoxy-4-hydroxycyclopent-2-ene is a known intermediate in such syntheses. (1S,4R) 1-acetoxy-4-hydroxycyclopent-2-ene has been prepared by a number of methods (see for example: Miura, S., et al., *Tetrahedron*, 1976, 32, 1893; Curran, T. T., et al., *Tetrahedron*, 1997, 53, 1983) including the enzymatic transesterification of 1,4-dihydroxycyclopent-2-ene using acetic acid esters and porcine pancreatic lipase or crude pancreatic extracts called pancreatin (Theil, F., et al., *Tetrahedron*, 1991, 47, 7569) to yield the 3S,5R monoacetate. The acetylations have generally been done with 2,2,2-trichloroethyl acetate as the acetylating agent and pancreatin as the enzyme. (Thiel, F., et al., *Synthesis*, 1988, 540–541; Thiel, F., et al. *Tetrahedron*, 1991, 47, 7569, 1991 and 47, 7569–7582). Subsequent procedures compared 2,2,2-trichloroethyl acetate with vinyl acetate and vinyl butyrate and also demonstrated the benefits of running the reactions in THF as the solvent with triethylamine as an additive to improve the selectivity. (Thiel, F., et al., *Liebigs Ann. Chem.*, 1991, 195–200). However, lot-to-lot variation of enzyme catalysts lead to variable results, produce significant amounts of diacetate, and the desired monoacetate has been reported to be isolated only by costly chromatography.

Accordingly, there is a need for a process for the production of (1S,4R) 1-acetoxy-4-hydroxycyclopent-2-ene which is consistent, provides enantiomerically enriched product of enantiomeric excess of >94%, produces a minimum amount of diacetate, consumes a minimum amount of vinyl acetate and allows isolation of the product by crystallization.

SUMMARY OF THE INVENTION

This invention provides a process for the preparation of (1S,4R) 1-acetoxy-4-hydroxycyclopent-2-ene comprising the steps of:

1) determining the water content of pancreatin;

2) mixing pancreatin, cis-1,4-dihydroxycyclopent-2-ene, vinyl acetate, and triethylamine in a solvent;

3) adjusting the water content of the mixture such that the water is 5–7% by weight relative to pancreatin; and 4) maintaining a reaction temperature of −40° C. to +40° C., preferably −5° C. to +10° C. with stirring until the reaction is substantially complete.

Alternatively, the step of adjusting the water content of the pancreatin may take place before adding the pancreatin to the mixture. Accordingly, the process also comprises the steps of:

1a) determining the water content of pancreatin;

2a) adjusting the water content of the pancreatin such that the water is 5–7% by weight relative to pancreatin;

3a) mixing pancreatin, cis-1,4-dihydroxycyclopent-2-ene, vinyl acetate, and triethylamine in a solvent; and 4a) maintaining a reaction temperature of −40° C. to +40° C., preferably −5° C. to +10° C. with stirring until the reaction is substantially complete.

The order of addition of water does not make a difference in the reaction to form (1S,4R) 1-acetoxy-4-hydroxycyclopent-2-ene. Once the reaction is substantially complete the (1S,4R) 1-acetoxy-4-hydroxycyclopent-2-ene may be isolated by the further steps of:

5) concentrating the reaction mixture at 20–50° C. bath temperature and 20–60 mm pressure;

6) dissolving the residue in methyl-t-butylether, optionally treating the mixture with activated charcoal and filtering the mixture; and 7) precipitating (1S,4R) 1-acetoxy-4-hydroxycyclopent-2-ene (Formula I) by the addition of a hydrocarbon solvent at 0–15° C.

DETAILED DESCRIPTION OF THE INVENTION

The present invention provides a process for the production of (1S,4R) 1-acetoxy-4-hydroxycyclopent-2-ene using pancreatin. Pancreatin is a semipurified enzyme mixture that undoubtedly contains many active enzymes, such as porcine pancreatic lipases (PPL). However, "pancreatin" gives better reactivity and selectivity than enzyme preparations sold as Porcine Pancreatic Lipase. The preferred pancreatin is prepared from hog pancreases although other pancreatic preparations could be used.

The first step in the process is determining the water content of pancreatin. The water content may be determined by methods well known to those skilled in the art. These methods include the Karl-Fischer titration, and measurement of weight loss after careful drying. The Karl-Fisher titration is preferred because of its greater speed, and because it is not certain that only water is lost on drying. The pancreatin may, at this point, either be mixed with cis-1,4-dihydroxycyclopent-2-ene (Formula II),

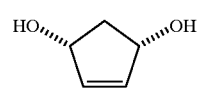

Formula II and triethylamine in a solvent, in which case the water content of the mixture is adjusted such that the water is 5–7% by weight relative to pancreatin. Alternatively, the step of adjusting the water content of the pancreatin may take place before adding the pancreatin to the mixture. In this case, the water content of the pancreatin is adjusted such that the water is 5–7% by weight relative to pancreatin, and then the pancreatin with its associated water is mixed with cis-1,4-dihydroxycyclopent-2-ene, vinyl acetate, and triethylamine in a solvent. Either order of addition of water leads to the same reaction mixture. The amount of pancreatin used in proportion to substrate is not fixed. The less pancreatin used, the slower the reaction. It has been found that approximately one gram of 8× pancreatin per gram of substrate provides a convenient ratio and allows the reaction to be substantially complete in 22–24 hours. Prancreatins of greater purity such as 10× may be used in proportionally lower amounts, while pancreatins of lower purity, such as 4×, may be used in proportionally larger amounts. One skilled in the art can readily determine what proportion of pancreatin relative to substrate to use, based upon the purity level of the pancreatin, and the speed of reaction desired. Vinyl acetate is used in molar excess compared to the starting material. A range of 5 to 7 moles of vinyl acetate per mole starting material is convenient. A level of 6 moles of vinyl acetate per mole starting material provides good results. The triethylamine is present in catalytic quantities. A range of 0.02 to 0.1 moles of triethylamine per mole starting material is convenient. A level of 0.05 moles of triethylamine per mole starting material provides good results.

After the starting material, the pancreatin, vinyl acetate, triethylamine, and the solvent are mixed, the reaction is run at a reaction temperature of −40° C. to +40° C., preferably −5° C. to +10° C., with stirring until the reaction is substantially complete. The reaction may be considered to be substantially complete when there is less than 5% diol in the product mixture. The progress of the reaction may be checked by methods known to those skilled in the art such as thin layer and liquid chromatography.

Once the reaction is substantially complete the (1S,4R) 1-acetoxy-4-hydroxycyclopent-2-ene may be isolated by the further steps of:

e) concentrating the reaction mixture at 20–50° C. bath temperature and 20–60 mm pressure;

f) dissolving the residue in methyl-t-butylether, optionally treating the mixture with activated charcoal and filtering the mixture;

g) precipitating (1S,4R) 1-acetoxy-4-hydroxycyclopent-2-ene (Formula I) by the addition of a hydrocarbon solvent, such as straight chain, branched chain or cyclic pentanes, hexanes, heptanes, octanes, and petroleum ether at 0–15° C.

The (1S,4R) 1-acetoxy-4-hydroxycyclopent-2-ene may be isolated from the methyl-t-butyl ether solution by the addition of a hydrocarbon solvent such as straight chain, branched chain or cyclic pentanes, hexanes, heptanes, octanes, and petroleum ether at 0–15° C. Rapid stirring and seeding are helpful in inducing crystal formation. Heptane at 30° C. to give a 3:1 ratio MTBE-heptane followed by cooling to 10° C. with periodical seeding and rapid stirring are preferred conditions. It was observed that if the freshly formed suspension of crystals was cooled below 0° C. their quality rapidly deteriorated due to the excessive containment of diacetate byproduct and a heavy oily coating. To eliminate these problems, it is useful to cool the solution down only to 0° C. and add an additional 125% of the initial heptane volume to the crystal suspension. Additionally, the crystal cake is washed with pre-cooled 0° C. heptane on a coarse fritted funnel. Using these techniques, a 60–70% yield of crystals with enantiomeric purity of 95–99% may be obtained.

The solvent for the reaction may be selected from ethers having boiling points of 34–150° C. Such ethers include ethyl ether, t-butyl methyl ether, furan, and tetrahydrofuran, 2-methyl-tetrahydrofuran, 2,5-dimethyl-tetrahydrofuran, diisopropyl ether, dipropyl ether, and dibutyl ether.

Filter aids may optionally be used in filtration steps. Suitable filter aids include diatomaceous earth, cellulose, magnesium silicate and the like.

It has been found that the enzyme preparations vary lot to lot, leading to differences in the rate of acetylation as well as selectivity. The water content of the enzyme is a major causative factor in the variability as shown in Table 1.

TABLE 1

| % water wt/wt pancreatin | time | diol | monoacetate | diacetate | monoacetate enantiomer |
|---|---|---|---|---|---|
| 3.0% | 8 hrs | 3.24% | 60.31% | 34.76% | 1.68% |
| 6.6% | 23 hrs | 2.41% | 76.74% | 19.65% | 1.27% |
| 12% | 48 hrs | 4% | 79.1% | 16.9% | not determined |

Optimum results are obtained with a water content of 5–7%. Larger amounts of water decrease the rate of the reaction and do not provide an improvement in selectivity between the mono-acetate and the di-acetate when a reasonable reaction endpoint (<5% diol) is obtained. With low water content, the reaction rate is greatly accelerated and the selectivity between the mono-acetate and the di-acetate decreases.

Another factor, which influences selectivity of the transesterification, is the concentration of the reaction. It has been found that the amount of diacetate formed increases as the dilution increases. Thus, at 0.2 molar concentration of the dihydroxycyclopentene, the ratio of monoacetate to diacetate product is 1 to 1, at 1 molar it is 3.3:2, and at 2 molar it is 3.6 to 2.

Other factors which influences the transesterification include the temperature of the reaction, use of pancreatin or lipase and the addition of varying amounts of triethylamine as shown in Table 2. Optimum conditions for the transesterification are the use of pancreatin at 5° C. with added triethylamine at a concentration of 2 molar of dihydroxycyclopentene. Results listed in Table 2 are from reactions conducted using the conditions described in the EXAMPLE.

TABLE 2

| Reaction Conditions | Proportion of | | | % ee | Time elapsed |
|---|---|---|---|---|---|
| | Mono-acetate | Di-acetate | Diol | | |
| Lipase 20° C. | 100 | 63 | 0 | 91.5 | 24 |
| 40° C. | 100 | 100 | 0 | 85.4 | 24 |
| Lipase 10° C. | 100 | 36 | 0 | 86.3 | 24 |
| Lipase 0° C. Lipase | 100 | 20 | 74 | 82.3 | 22 |
| | 100 | 20 | 0 | | |
| | 100 | 20 | 51 | 85 | 26 |
| | 100 | 20 | 0 | | |
| | 100 | 22 | 11 | 92.8 | 48 |
| | 100 | 22 | 0 | | |

TABLE 2-continued

| Reaction Conditions | Proportion of | | | % ee | Time elapsed |
|---|---|---|---|---|---|
| | Mono-acetate | Di-acetate | Diol | | |
| 10° C. | 100 | 27 | 27 | 85.4 | 22 |
| Lipase | 100 | 28 | 15 | 88.9 | 26 |
| | 100 | 28 | 0 | | |
| | 100 | 32 | 0 | 94.02 | 48 |
| 5%, Et₃N, | 100 | 50 | 7 | 87.8 | 16 |
| 20° C. | 100 | 50 | 0 | | |
| Lipase | 100 | 55 | 0 | 92.9 | 23 |
| 5%, Et₃N, | 100 | 26 | 13 | 90.4 | 23 |
| 5° C., Lipase | 100 | 25 | 0 | | |
| | 100 | 28 | 5 | 93.9 | 30 |
| | 100 | 28 | 0 | | |
| 25%, Et₃N, | 100 | 25 | 36 | 82.9 | 16 |
| 5° C., Lipase | 100 | 25 | 0 | | |
| | 100 | 26 | 16 | 88.8 | 22 |
| | 100 | 27 | 0 | | |
| | 100 | 32 | 0 | 97.7 | 40 |
| pancreatin 20° C. | 100 | 48 | 0 | 92.1 | 23 |
| pancreatin 5° C. | 100 | 20 | 21 | 90.9 | 22 |
| pancreatin 5° C., 5% Et₃N | 100 | 23 | 0 | 96.2 | 22 | e.e. = % major isomer − % minor isomer

Without further elaboration, one skilled in the art can, using the preceding description, practice the present invention to its fullest extent. The following detailed EXAMPLE describes how to prepare the compound and perform the various processes of the invention and is to be construed as merely illustrative, and not a limitation of the preceding disclosure in any way whatsoever.

EXAMPLE

Preparation of (1S,4R) 1-acetoxy-4-hydroxycyclopent-2-ene a) pancreatin (Sigma # P-7545, 8x USP) was assayed for water using standard Karl-Fisher titration and determined to be 4.4%;

b) pancreatin (39.16 g), cis-1,4-dihydroxycyclopent-2-ene (40 g, Johnson, C. R., et al., U.S. Pat. No. 4,873,360), vinyl acetate (221 mL) and triethylamine (2.8 mL) were dissolved in 200 mL of tetrahydrofuran;

c) water (0.84 g) was added to bring the water to 6.5% by weight of the pancreatin;

d) the mixture was cooled to 5° C. and stirred for 23 hours;

e) the reaction mixture was filtered through diatomaceous earth (celite), the filter cake washed with tetrahydrofuran (50 mL) and the filtrates concentrated at 40° C. bath temperature and 40–60 mm pressure;

f) the residue was dissolved in methyl-t-butylether (200 ml), activated charcoal (18 g) was added and the mixture filtered through diatomaceous earth and concentrated at 40° C. bath temperature and 40–60 mm pressure;

g) the oil of step f) was dissolved in methyl-t-butyl ether (80 mL) and filtered through magnesium silicate (magnesol), the magnesol washed with additional methyl-t-butyl ether, and the combined filtrates warmed to 30° C.;

h) heptane (75 mL) was added to the solution of step g) in small portions and the mixture cooled to 10° C. with stirring and seeding;

i) after crystallization occurred, the mixture was cooled to 0° C., additional heptane (100 mL) added, and the mixture stirred 1 hour; and j) the crystals were filtered, washed with cold (0° C.) heptane (100 ml) and dried to give (1S,4R) 1-acetoxy-4-hydroxycyclopent-2-ene in approximately 70% yield and with enantiomeric excess of >98%.

What is claimed is:

1. A process for the preparation of enantiomerically enriched (1S,4R) 1-acetoxy-4-hydroxycyclopent-2-ene comprising the steps of:

a) determining the water content of pancreatin;

b) mixing pancreatin, cis-1,4-dihydroxycyclopent-2-ene, vinyl acetate, and triethylamine in tetrahydrofuran;

c) adjusting the water content of the mixture such that the water content is 5–7% of the weight of the pancreatin;

d) maintaining a reaction temperature of −40° C. to +40° C. with stirring until the reaction is substantially complete;

e) concentrating the reaction mixture f) dissolving the residue in methyl-t-butylether, optionally treating the mixture with activated charcoal and filtering the mixture; and g) precipitating (1S,4R) 1-acetoxy-4-hydroxycyclopent-2-ene with an enantiomeric purity of 95–99% by the addition of a hydrocarbon solvent at 0–15° C.

2. A process for the preparation of enantiomerically enriched (1S,4R) 1-acetoxy-4-hydroxycyclopent-2-ene comprising the steps of:

a) determining the water content of pancreatin;

b) adjusting the water content of the mixture such that the water content is 5–7% of the weight of the pancreatin;

c) mixing pancreatin, cis-1,4-dihydroxycyclopent-2-ene, vinyl acetate, and triethylamine in tetrahydrofuran;

d) maintaining a reaction temperature of −40° C. to +40° C. with stirring until the reaction is substantially complete;

e) concentrating the reaction mixture f) dissolving the residue in methyl-t-butylether, optionally treating the mixture with activated charcoal and filtering the mixture; and g) precipitating (1S,4R) 1-acetoxy-4-hydroxycyclopent-2-ene with an enantiomeric purity of 95–99% by the addition of a hydrocarbon solvent at 0–15° C.

3. A process according to claim 1 or claim 2 wherein the reaction temperature of step (d) is maintained between +5° C. to +10° C.

4. A process according to claim 1 or claim 2 wherein step (e) concentrating the reaction mixture is performed at 20–50° C. bath temperature and 20–60 mm Hg pressure.

* * * * *